United States Patent [19]
Onuschak et al.

[11] Patent Number: 6,139,912
[45] Date of Patent: Oct. 31, 2000

[54] METHOD FOR INTERMITTENT APPLICATION OF PARTICULATE MATERIAL

[75] Inventors: Anthony David Onuschak, Dayton; Fernando Ydoate, Flemington, both of N.J.

[73] Assignee: McNeil-PPC, Inc., Skillman, N.J.

[21] Appl. No.: 09/309,411

[22] Filed: May 10, 1999

[51] Int. Cl.[7] ....................................................... B05D 1/30
[52] U.S. Cl. ............................... 427/180; 427/197; 222/1
[58] Field of Search ..................................... 427/180, 188, 427/197, 286, 288; 118/308, 312; 264/131, 518; 239/99; 222/1, 548–555

[56] References Cited

U.S. PATENT DOCUMENTS

| | | |
|---|---|---|
| 4,130,268 | 12/1978 | Kojima et al. . |
| 4,138,161 | 2/1979 | Payne . |
| 4,696,253 | 9/1987 | Frei et al. . |
| 4,800,102 | 1/1989 | Takada . |
| 5,558,713 | 9/1996 | Siegfried et al. . |
| 5,614,147 | 3/1997 | Pelley . |
| 5,750,066 | 5/1998 | Vonderhaar et al. . |

*Primary Examiner*—Fred J. Parker
*Attorney, Agent, or Firm*—James P. Barr; Martha Taylor

[57] ABSTRACT

The present invention is directed to a method and apparatus for intermittently applying particulate material to a substrate. A continuous supply of particulate material is provided from a supply source to a valve having a powder application phase and a recycle phase. The valve is disposed to the powder application phase to allow particulate material to pass therethrough and to fall freely onto at least a portion of the substrate. The valve is disposed in the recycle phase to prevent dispensing of the particulate material onto the substrate and to retain the particulate material within the valve to be conveyed back to the supply source.

11 Claims, 14 Drawing Sheets

METHOD FOR INTERMITTENT APPLICATION OF PARTICULATE MATERIAL

FIELD OF THE INVENTION

The present invention relates to a novel method and apparatus for intermittently applying particulate material to a substrate with accurate placement within the substrate.

BACKGROUND OF THE INVENTION

Absorbent structures are known for inclusion in disposable absorbent articles used for absorbing body fluids and other exudates. Such absorbent structures have traditionally been made from readily available and relatively inexpensive materials such as cotton fibers, wood pulp fluff, cellulosic tissue or wadding, or other absorbent fibers. These materials have provided satisfactory absorbency of fluids both in terms of absorbency rate and overall absorbent capacity. Unfortunately, absorbent structures made from such materials may tend to collapse when wetted, thereby losing some of their void volume. Such structures may also allow absorbed fluid to be squeezed back out of the structure onto the user of the absorbent article. Furthermore, when such structures have absorbed fluid, they may present an uncomfortable wet feeling against the skin of the user.

More recently, superabsorbent polymer particles have been combined with the more traditional absorbent materials to provide structures with enhanced absorbency and retention, which may help to eliminate the problems of squeeze-out and wet surface feel. Replacement of traditional absorbent materials with superabsorbent polymer particles may also allow for absorbent products to be thinner while retaining the absorbent capacity of thicker, bulkier products. A drawback to superabsorbent polymer particles, however, is their relatively high cost compared to the more traditional absorbent materials.

Additionally, since superabsorbent polymer particles tend to swell as they absorb fluid, they may cause what is commonly known as gel-blocking. In other words, as fluid is absorbed by the particles of superabsorbent polymer, those particles swell and may form an occlusive layer of swollen superabsorbent particles. This occlusive layer then prevents the passage of additional fluid into the structure. Thus, the superabsorbent polymer particles must be properly placed within an absorbent structure to allow for this swelling and to most fully utilize their absorbent capacity. Generally, prevention of gel-blocking has been realized by mixing superabsorbent polymer particles with spacer materials, such as absorbent or nonabsorbent fibers, or by placing the superabsorbent polymer particles toward the bottom of the absorbent structure. However, although these methods of superabsorbent polymer placement may minimize gel-blocking, they do not effect the most efficient use of the superabsorbent polymer's absorbent capacity.

It may often be desirable to add other particulate or powder materials to absorbent structures to provide such benefits as odor control, enhanced dryness, skin protection or treatment, or a clean appearance. Examples of such particulate or powder materials include, without limitation, zeolites, sodium bicarbonate, microencapsulated perfumes and other compounds, titanium dioxide, and absorbent or superabsorbent fibers. Unfortunately, most of these types of particulate materials are higher in cost than traditional absorbent materials, and therefore, it is desired to accurately place precise amounts of these particulate materials within the article so that they are fully utilized with minimum waste and minimum cost.

Therefore, what is needed is an absorbent structure with good absorbency and retention of fluid. What is also needed is an absorbent structure which will help to provide a dry feel to the skin of a user when used in an absorbent article. What is further needed is an absorbent structure with superabsorbent polymer particles or other particulate materials spaced and placed within the structure to most fully utilize the unique capabilities of particles, and a method and apparatus for making such an absorbent structure.

SUMMARY OF THE INVENTION

It is an object of the present invention to provide a method and apparatus for intermittently applying a particulate material to a substrate.

It is a further object of the present invention to provide a method and apparatus for intermittently applying a precise amount of a particulate material to a substrate.

It is another object of the present invention to provide a method and apparatus for intermittently applying a particulate material to a substrate accurately within the boundaries of a predetermined pattern.

It is yet another object of the present invention to provide a method of making an absorbent structure with superabsorbent polymer particles spaced and placed within the structure to most fully utilize the absorbency and retention capabilities of the superabsorbent polymer particles.

In accordance with the present invention, there has been provided a method and apparatus for intermittently applying a precise quantity of a particulate material to a substrate accurately within the boundaries of a predetermined pattern with minimal waste of the particulate material.

Further in accordance with the present invention, there has been provided a method and apparatus for making a novel absorbent structure for use in absorbent articles. The absorbent structure includes an absorbent element formed from absorbent fibers and may optionally include additional laminate layers such as one or more layers of a nonwoven fabric. The nonwoven fabric may have a lower density and a higher porosity than the absorbent element of the invention to allow for fluid acquisition and the transfer of the acquired fluid to an adjacent, higher density absorbent element. Alternatively, the nonwoven fabric may have a higher density and a lower porosity than the absorbent element to increase fluid wicking throughout the nonwoven fabric. Preferably, lower-density nonwoven fabrics are placed adjacent the body-facing surface of an absorbent element, and higher-density nonwoven fabrics are placed adjacent the garment-facing surface of an absorbent element.

The absorbent element has a center region surrounded by peripheral edges. The absorbent element has an upper surface and a lower surface defining therebetween an element thickness. The element thickness has an upper 35% and a lower 65%. The absorbent element is an integral structure having a zone of high absorbency which comprises an integral mixture of absorbent fibers and superabsorbent polymer particles and has a first surface and a second surface separated by a zone thickness. As used herein, the terminology "integral" means a unitary structure wherein the absorbent fibers are intermeshed throughout the entire absorbent element. Thus, there are no identifiable laminate layers which are separable from other layers within the element.

The high absorbency zone is located in at least a portion of the center region in the upper 35% of the absorbent element. The first surface of the high absorbency zone may optionally be coplanar with the upper surface of the absorbent element, or alternatively, the high absorbency zone may be below the upper surface of the absorbent element. The thickness of the high absorbency zone comprises about 35% of the thickness of the absorbent element, the remaining 65% of the absorbent element being substantially free of superabsorbent particles. Thus, the absorbent element comprises an upper high absorbency zone containing absorbent fibers and superabsorbent polymer particles located in an upper 35% of the thickness of the absorbent element and a lower absorbent region which is substantially free of super absorbent particles.

In a preferred embodiment, the superabsorbent polymer particles may be mixed with absorbent fibers within the high absorbency zone. In a most preferred embodiment, the superabsorbent polymer particles are uniformly and homogeneously mixed with the absorbent fibers within the high absorbency zone. Alternatively, the superabsorbent particles may be located within the high absorbency zone in a relatively narrow region comprising 15%, or more preferably 10%, of the absorbent element thickness. Additionally, the superabsorbent particles may be distributed within the high absorbency zone on an increasing gradient wherein the concentration of superabsorbent particles increases from the first surface of the high absorbency zone to the second surface of the high absorbency zone, or a decreasing gradient, wherein the concentration of superabsorbent particles decreases from the first surface of the high absorbency zone to the second surface of the high absorbency zone. In a most preferred embodiment the upper surface of the absorbent element is substantially free of superabsorbent particles, the high absorbency zone being slightly below the upper surface of the absorbent element wherein the upper surface of the absorbent element comprises 100% absorbent pulp fibers.

The absorbent structure is useful in absorbent articles such as sanitary napkins, diapers, incontinence articles and the like. An example of such an article comprises the absorbent element of the invention contained between a liquid-permeable body-facing layer and a liquid-impermeable barrier layer and positioned such that the body-facing layer is adjacent the upper surface of the absorbent element and the impermeable barrier layer is adjacent the lower surface of the absorbent element.

DETAILED DESCRIPTION OF THE INVENTION

Further characteristics and advantages of the invention will become clear from the following detailed description, appended drawings, and non-limiting examples.

The present invention is directed to a novel method and apparatus for intermittently applying particulate material to a substrate to make, for example, absorbent articles such as sanitary napkins having an absorbent structure which includes an absorbent element having an integral high absorbency zone located in an upper 35% of the absorbent element thickness. The absorbent articles will generally have a body-facing, liquid permeable cover layer, a garment-facing, liquid-impermeable barrier layer, and an absorbent structure between the body-facing layer and the barrier layer. The absorbent structure may optionally include a multi-layer laminate structure having one or more layers of nonwoven fabrics, such as fluid transfer layers in addition to the absorbent element. In a preferred embodiment, the absorbent structure comprises an upper, body-facing fluid transfer layer and a lower, absorbent element between the fluid transfer layer and the barrier layer, wherein the fluid transfer layer preferably has a porosity that is greater than the porosity of the absorbent element.

The absorbent element has a center region surrounded by peripheral edges. The absorbent element further has an upper surface and a lower surface defining therebetween an absorbent element thickness. The absorbent element thickness has an upper 35% and a lower 65%. The absorbent element has a high absorbency zone with a first surface and a second surface separated by a high absorbency zone thickness (hereinafter "zone thickness") comprising less than about 35% of the absorbent element thickness and being located in at least a portion of the center region in the upper 35% of the absorbent element thickness. The high absorbency zone comprises superabsorbent polymer particles and absorbent fibers. The lower 65% of the absorbent element thickness is substantially free of superabsorbent particles.

The novel absorbent structure made by the method and apparatus of the present invention is intended for use in disposable absorbent articles. These articles are adapted to be worn by a user in direct contact with the body for the purpose of absorbing body fluids and are subsequently thrown away after a single use.

Figure 1:
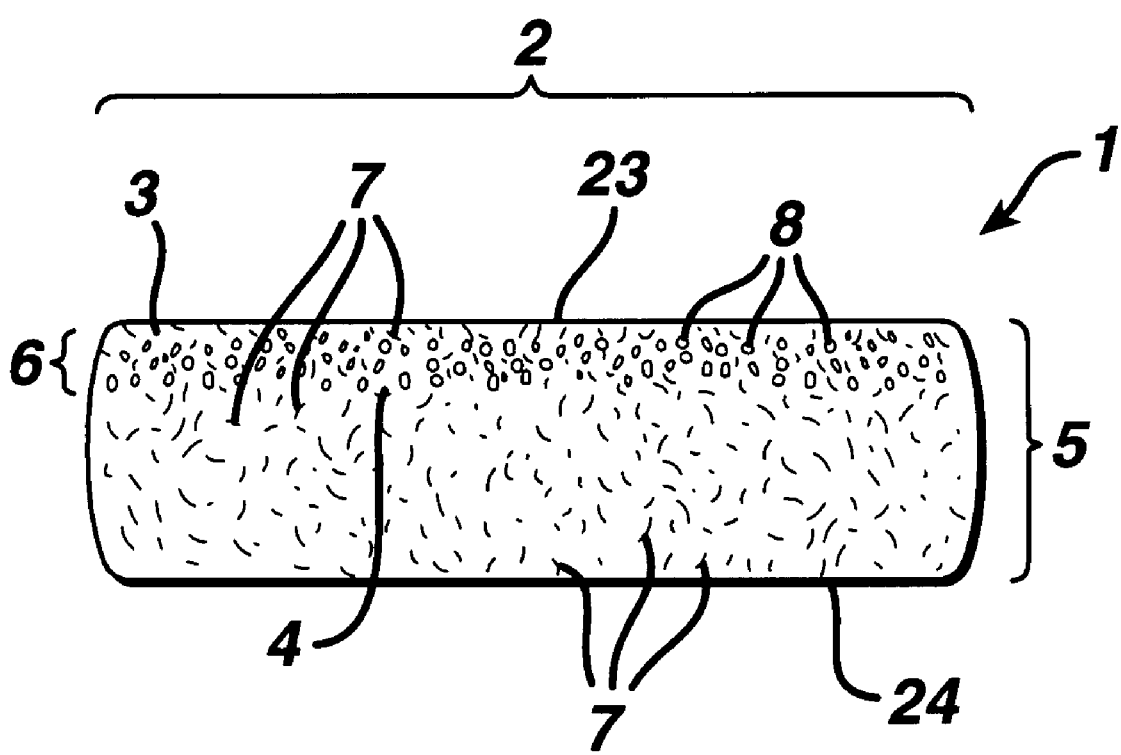
FIG. 1 is a sectional view of a first preferred embodiment of an absorbent element made by the method and apparatus of the invention.

Referring to FIG. 1, there is shown a sectional view of a first preferred embodiment of an absorbent element 1 made by the method of the present invention. FIG. 1 shows an integral absorbent element 1 with high absorbency zone 2 having a first surface 3 and a second surface 4 separated from one another by a thickness 6. The absorbent element has thickness 5 between an upper surface 23 and a lower surface 24. The high absorbency zone comprises absorbent fibers 7 and superabsorbent polymer particles 8. The superabsorbent polymer particles 8 are substantially contained within the high absorbency zone 2 in thickness region 6. It can be seen in the preferred embodiment illustrated by FIG. 1 that the upper surface 23 is substantially free of superabsorbent polymer particles 8, and that the superabsorbent polymer particles 8 are mixed with absorbent fibers 7 in the high absorbency zone 2 throughout thickness 6.

The absorbent fibers of the present absorbent element may comprise any absorbent fiber known in the art, including without limitation, naturally occurring fibers or synthetic fibers. Examples of naturally occurring absorbent fibers are wood pulp, cotton, silk, hemp and the like, while examples of synthetic absorbent fibers include without limitation rayon fibers, individualized crosslinked cellulose fibers, acrylic fibers, and the like. A preferred absorbent fiber for the absorbent element of the invention is wood pulp fluff.

For the purposes of the present invention, the term "superabsorbent polymer" refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N TYPE II™, and the product offered by Chemdal International, Inc. of Palatine, Ill., under the designation of 2100A™.

The absorbent elements made according to the method of the present invention may also comprise other absorbent of nonabsorbent materials, such as binders, nonabsorbent fibers, odor controlling particles, or perfumes. Examples of suitable binder materials include without limitation, ethylene vinyl acetate based latex binders, adhesives, and thermally fusible fibers, such as bicomponent fibers. Examples of suitable nonabsorbent fibers include without limitation, polyester fibers, polyolefin fibers, and bicomponent fibers.

Absorbent elements made according to the method of the present invention are commonly formed by air-laying the fibers and superabsorbent polymer particles. A preferred method of forming a preferred embodiment of the absorbent element of the invention involves first forming pulp fluff from a pulp board in a hammer mill or similar equipment designed to fiberize or separate and "open" the pulp fibers in the board. The separated pulp fibers are then entrained in an air stream and deposited on a foraminous surface to form a pulp batt or pad. The pulp batt or pad thus formed is a collection of individual fibers in a very loose configuration. The fibrous batt is substantially uncompressed, leaving spaces between the fibers that comprise the batt. Superabsorbent polymer particles that are added to the loose batt fall into these spaces between the fibers. The superabsorbent polymer particles may be added to a portion of the air-entrained fibers for deposition substantially throughout the thickness of the high absorbency zone. Alternatively, the superabsorbent polymer particles may be deposited directly onto a formed pulp batt at a desired point in the pulp deposition process to ensure that the superabsorbent particles are located at the desired narrow zone within the thickness of the structure. In the former case, the particles are mixed with pulp fibers throughout the high absorbency zone of the integral absorbent structure. In the latter case, the particles fall into the spaces between the fibers to form a fairly concentrated high absorbency zone within the integral absorbent structure with fibers separating the particles. In either case, the particles are separated by fibers. Finally, in a preferred embodiment, pulp fibers are laid over the top of the high absorbency zone so that the upper surface of the absorbent element is substantially free of superabsorbent polymer particles. In all cases, however, the superabsorbent polymer particles are substantially separated from one another by intermeshed pulp fibers within the high absorbency zone to maintain the integral configuration of the absorbent element.

The high absorbency zone located adjacent the upper surface of the absorbent element may extend across the entire upper surface of absorbent element or alternatively, may be confined to a particular localized region of the absorbent element, such as for example, being located solely in a central region and spaced inwardly away from the longitudinal edges or transverse end regions of the absorbent element. Alternatively, the high absorbency zone may comprise a plurality of spaced-apart longitudinally oriented stripes. Alternatively, the high absorbency zone may comprise two or more laterally oriented stripes extending along the end edges of the absorbent element or across the center of the absorbent element. In yet another embodiment, the high absorbency zone may comprise multiple discrete regions substantially separated from one another.

The thickness of the absorbent structure may be uniform throughout the expanse of the absorbent element or, for the purpose of specific fit, flexibility and absorbency requirements, the absorbent structure may have a tapered profile wherein certain areas of the structure, such as a central region, are thicker than other areas.

Figure 2:
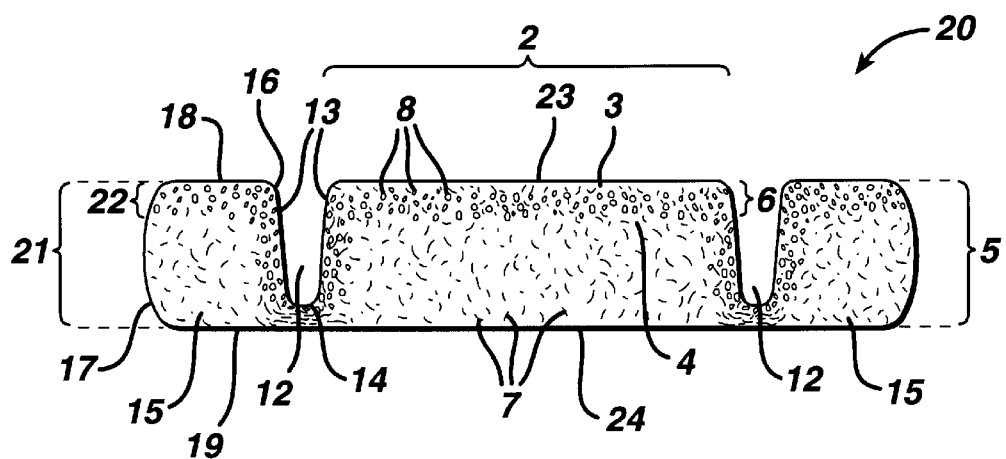
FIG. 2 is a sectional view of a second preferred embodiment of an absorbent element made by the method and apparatus of the invention.
Figure 4:
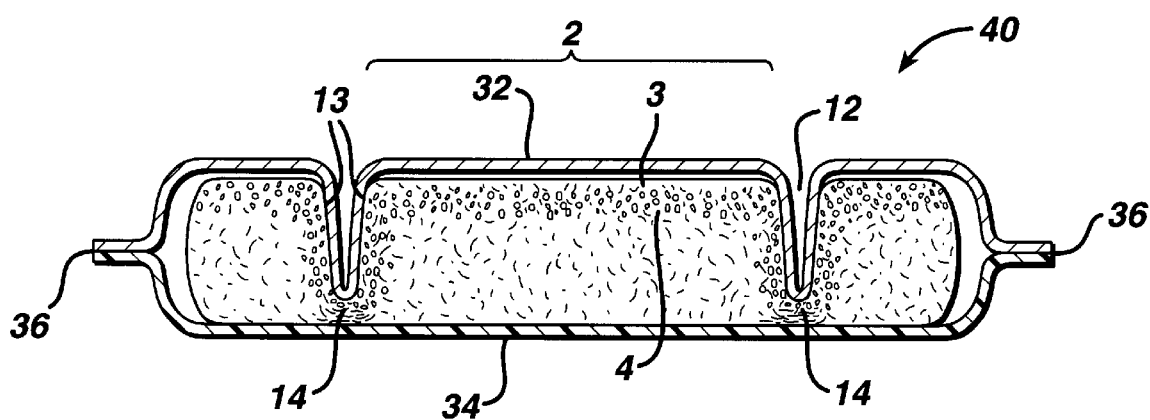
FIG. 4 is a sectional view of a second preferred embodiment of an absorbent article made by the method and apparatus of the invention.

As shown in FIGS. 2 and 4, the high absorbency zone may be surrounded by boundaries, such as densified channels. In this embodiment, the high absorbency zone comprises about 35% of the thickness of the absorbent element and is completely contained in a centrally located region between the channels. While the high absorbency zone may extend into the densified channels, it is preferred that the channels be substantially free of superabsorbent particles. The boundaries may also comprise other structural elements, such as raised areas measuring a greater thickness or caliper than the surrounding areas; repellent-treated area; embossed or depressed areas measuring a lesser caliper or thickness than the surrounding areas; colored areas having inks or other coloring agents printed thereon or being otherwise treated to exhibit a color that is visually perceptible as different from the color of the surrounding areas; or the edges of the absorbent structure. Alternatively, the top surface of the structure may be partially covered by a film or other impermeable material, leaving only a central opening uncovered. In such a case, this central opening would be the high absorbency zone.

An important feature of the method of the present invention is that it produces an absorbent structure, wherein the entire absorbent element, including the high absorbency zone, is an integral structure with accurate and precise placement of the superabsorbent within the high absorbency zone. In other words, the superabsorbent-containing high absorbency zone is not present as a separate layer within the absorbent element; rather, it is simply a region within the absorbent element. The absorbent fibers that comprise the absorbent element are continuously intermingled with the absorbent fibers that comprise the high absorbency zone and no discernible laminate or separate structure is present. An advantage of this integral type of structure is that it remains a single whole element during the absorption of fluid, and it is not subject to delamination or gapping as fluid is absorbed. Such gapping or delamination disrupts the fluid transport and distribution capabilities of the structure and may diminish its overall absorbency. An integral absorbent element also allows for a simpler process of absorbent article construction.

The absorbent element shown in FIG. 2 is an alternative embodiment of an absorbent element made according to the method of the present invention. The structure 20 of FIG. 2 shows an integral absorbent element comprising a high absorbency zone 2 with a first surface 3 and a second surface 4 separated from one another by a thickness 6. The absorbent element has thickness 5 and high absorbency zone 2 with zone thickness 6 adjacent the first surface. The absorbent element comprises absorbent fibers 7 and superabsorbent polymer particles 8. The superabsorbent polymer particles 8 are substantially contained within the high absorbency zone thickness 6. It can be seen in the embodiment illustrated by FIG. 2 that the upper surface 23 is substantially free of superabsorbent polymer particles 8, and that the superabsorbent polymer particles 8 are mixed with absorbent fibers 7 in the high absorbency zone thickness 6. FIG. 2 also shows the presence of two densified channels 12, which may be compressed into the absorbent structure after its formation. Each channel 12 has inner edges 13 and a lowermost portion or bottom 14. The channels define the high absorbency zone therebetween. Side portions 15 of the element include those portions of the element that are outboard of channels 12, or those portions of the article that are between the top 16 of the channel and the outside edge 17 of the element. These side portions 15 may contain superabsorbent or they may be free of superabsorbent. Each side portion 15 shown in FIG. 2 comprises a top surface 18 and a bottom surface 19 separated from one another by a side portion thickness 21. The side portion thickness 21 may be substantially equivalent to the high absorbency zone thickness 6, as shown in FIG. 2; however, side portion thickness 21 may be substantially more or less than high absorbency zone thickness 6.

The side portion thickness 21 may comprise a second high absorbency zone thickness 22 adjacent the top surface 18. The second high absorbency zone 22 comprises 35% of the side portion thickness 21. As shown in FIG. 2, each side portion 15 comprises absorbent fibers 7 and superabsorbent polymer particles 8, wherein the superabsorbent polymer particles 8 are substantially contained within the second region 22.

Figure 3:
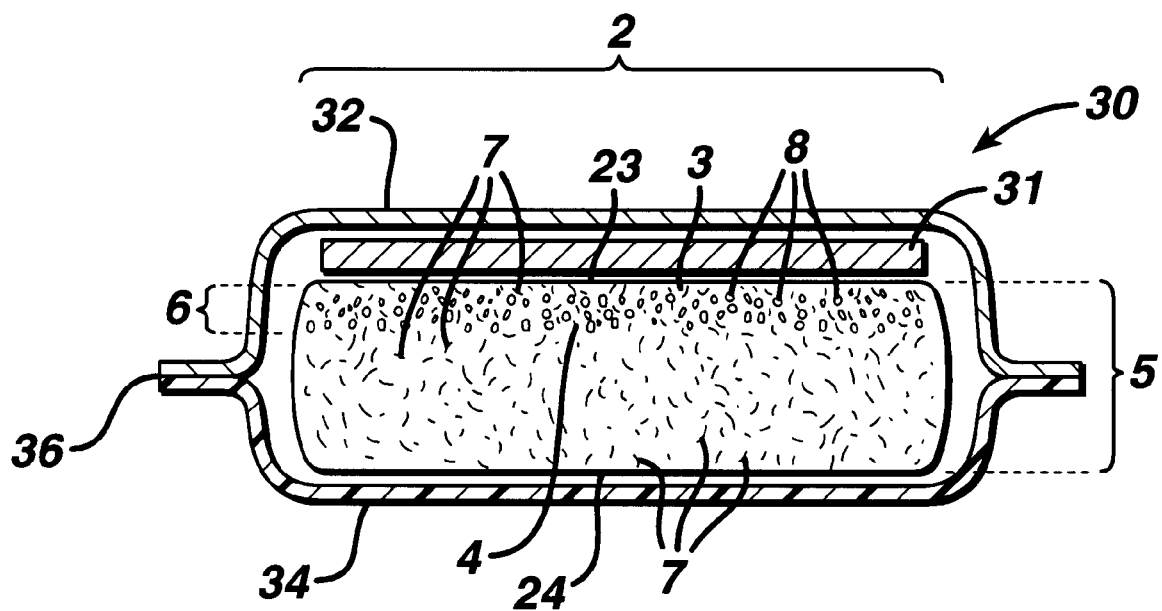
FIG. 3 is a sectional view of a first preferred embodiment of an absorbent article made by the method and apparatus of the invention.

The absorbent article 30 shown in FIG. 3 is a sectional view of a first preferred embodiment of an absorbent article made according to the method of the present invention. The absorbent article 30 of FIG. 3 has an integral absorbent element comprising a high absorbency zone 2 with a first surface 3 and a second surface 4 separated from one another by a thickness 6. The absorbent element comprises absorbent fibers 7 and superabsorbent polymer particles 8. The superabsorbent polymer particles 8 are substantially contained within the high absorbency zone thickness 6. It can be seen in the preferred embodiment illustrated by FIG. 3 that the upper surface 23 is substantially free of superabsorbent polymer particles 8, and that the superabsorbent polymer particles 8 are mixed with absorbent fibers 7 in the high absorbency zone thickness 6. The integral absorbent element is positioned between a body-facing layer 32 and a barrier layer 34 such that the upper surface 23 is adjacent the body-facing layer 32. The body-facing layer 32 and the barrier layer 34 are joined to one another around the periphery of the absorbent element to form what is commonly known as a flange seal.

The absorbent article 40 shown in FIG. 4 is a sectional view of a second preferred embodiment of an absorbent article made according to the method of the present invention. The absorbent article 40 of FIG. 4 has an integral absorbent element comprising a high absorbency zone 2 with a first surface 3 and a second surface 4 separated from one another by a thickness 6, essentially as shown in FIG. 2 and described in detail above. As shown in FIG. 4, the integral absorbent element of FIG. 2 is positioned between a body-facing layer 32 and a barrier layer 34 such that the upper surface 23 is adjacent the body-facing layer 32. The body-facing layer 32 follows the shape of the first surface to line the inner edges 13 of the channels. The body-facing layer 32 may be connected or secured to the bottom 14, or lowermost portion, of the channel 12, as shown in FIG. 4.

The body-facing layer 32 and the barrier layer 34 are joined to one another around the periphery of the absorbent element to form what is commonly known as a flange seal 36.

Although the articles 30 and 40 shown in FIGS. 3 and 4 respectively have the body-facing layer 32 and the barrier layer 34 joined together by a flange seal 36, this is for illustrative purposes only. The presence of a flange seal is not necessary to achieve the benefits and advantages of the article made according to the method of the invention. Alternatively, the body-facing layer of the absorbent article may be wrapped completely around the absorbent element and overlapped and sealed to itself on the underside of the article. The barrier layer may be present either between the absorbent element and the overlapped portion of the body-facing layer, or on the outer surface of the overlapped portion of the body-facing layer. Other methods of securing a body-facing layer and a barrier layer to an absorbent article structure will be apparent to those who are familiar with the construction of absorbent articles.

The body-facing cover layer may comprise any soft, flexible, porous material which allows fluid to pass therethrough, and may, for example, be comprised of a nonwoven fibrous sheet or an apertured or perforated plastic film. Examples of suitable nonwoven fibrous sheets include without limitation, carded webs, spunbond webs, meltblown webs, random-laid webs, and the like. The fibers comprising such webs may comprise polyester, polyethylene, polypropylene, rayon, or combinations of these. The webs may further comprise bonding agents, surfactants, or other treatments. A preferred material for the body-facing layer of the invention is a homogeneous blend of high denier polypropylene staple fibers and low denier polypropylene staple fibers. The high denier staple fibers and the low denier staple fibers preferably differ by 2 denier, where the low denier staple fibers preferably have a denier of about 3 and the high denier staple fibers preferably have a denier of about 5. The high denier staple fibers are present in the non-woven fabric in an amount of from 40 to 60 weight percent. The low denier staple fibers are present in the non-woven fabric in an amount of from 40 to 60 weight percent based on the total weight of the non-woven fabric.

The barrier layer is a liquid-impermeable layer, and may comprise any flexible material that prevents the transfer of fluid but does not necessarily prevent the passages of gases. Commonly used materials are polyethylene or polypropylene films. Other suitable polymeric film materials tat may be used as impermeable barriers include, but are not limited to polyesters, polyamides, polyethylene vinyl acetate, polyvinyl chloride, and polyvinylidene chloride, and the like and combinations thereof. Co-extruded and laminated combinations of the foregoing, wherein such combinations are permitted by the chemical and physical properties of the film, may be used. Fluid impermeable foams and repellent treated papers may also be used. Films that are fluid barriers, but permit gases to transpire, i.e., "breathable films", may be used. These may be chosen from polyurethane films and from micro-porous films, where micro-porosity is created by ionizing radiation or by leaching out of soluble inclusions using aqueous or non-aqueous solvents. Fabrics whose surfaces have been made repellent or whose pores are small by virtue of close packing of fibers, or whose pores have been reduced in size by closing off large liquid admitting pores, may also be used alone, or together with breathable films, as breathable barriers.

A suitable backing sheet material can be an opaque polyolefin, e.g., polyethylene, web impermeable to body fluids and about 0.001 inch thick. Another suitable sheet material for this purpose is a polyester, e.g., polyethylene terephthalate, web having a thickness of about 0.0005 inch.

Figure 6:
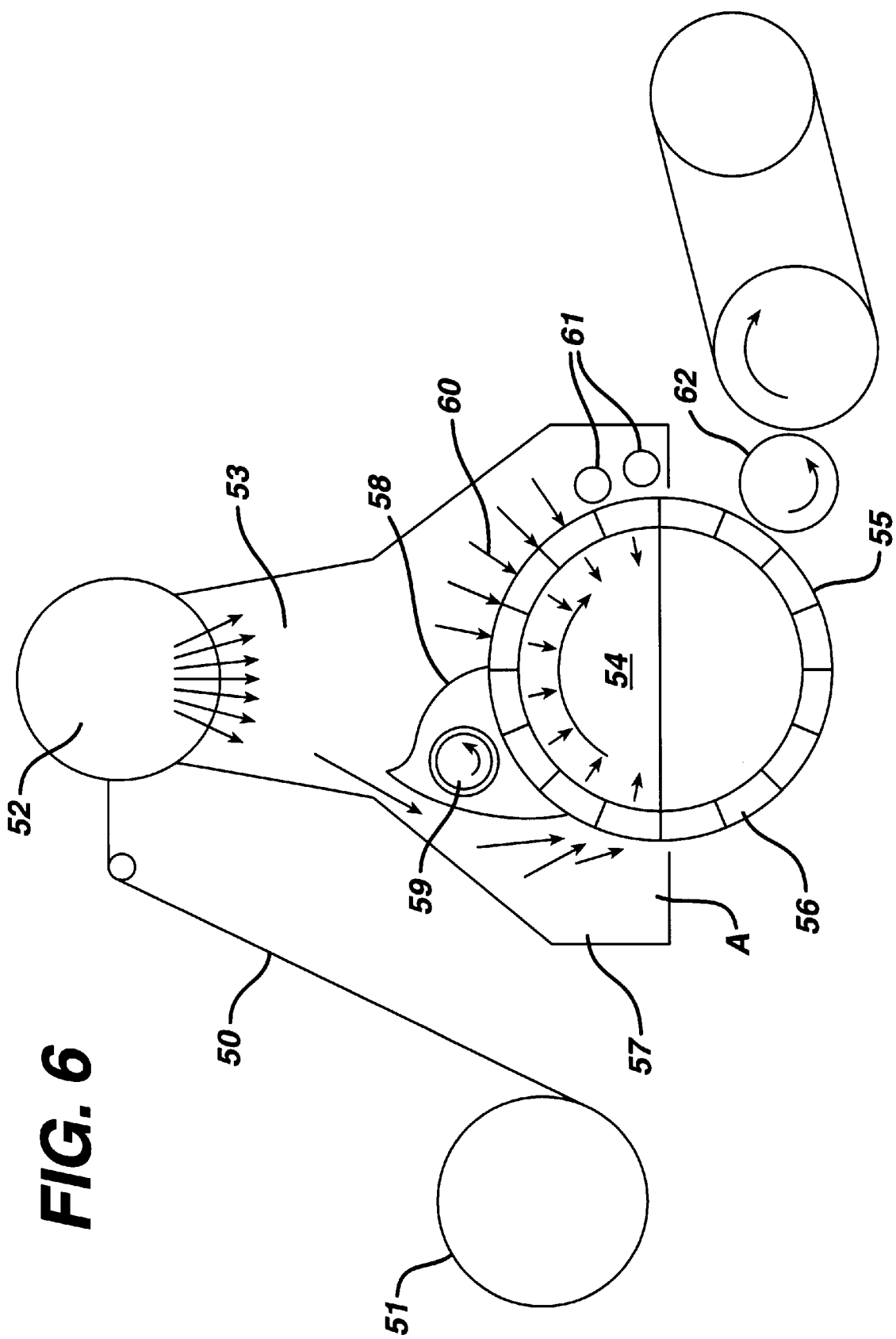
FIG. 6 is a schematic illustration of a preferred embodiment of the apparatus of the invention.

A preferred apparatus for making the absorbent structure of the invention is illustrated in FIG. 6. With reference to FIG. 6, an absorbent may be prepared according to the following method. While any of the absorbent fibers as previously discussed may be used to form the absorbent element, for purposes of illustration, wood pulp fibers are used to describe the preferred method and apparatus. The wood pulp of the absorbent element is supplied in raw material form as a compressed sheet, or pulp board 50, that is wound on a roll. The pulp unwind 51 allows the board to be fed into a pulp mill 52, where a high speed hammer rotor opens the board into substantially individual wood pulp fibers of about 2.5 mm average length, commonly known as pulp fluff or ground wood pulp. Air is pulled through the pulp mill and the adjacent forming chamber 53 by a forming wheel vacuum 54. This air conveys the pulp fluff to the forming wheel 55 and into the molds 56. The molds are cavities in the forming wheel surface spaced around the circumference of the forming wheel. The bottom of the molds consist of a porous screen to allow the air to be pulled through the molds, leaving the pulp fluff deposited on the screen.

The molds are mounted on the forming wheel which rotates clockwise. When the molds first enter the forming chamber at position A, they are empty. In the initial fiber deposition zone 57, 100% pulp fibers are deposited on the bottom of the molds 56. The thickness of the pulp deposited in the initial fiber deposition zone comprises 5% to 25% of the final thickness of the absorbent element, and it acts as a filter to hold the granular superabsorbent polymer particle that will be deposited in the mold. The boundaries of the initial fiber deposition zone 57 are formed by the left side of the forming chamber 53 and the left side of the seal for the particle application zone 58.

The particle application zone 58 comprises a rotary particle applicator valve 59 that dispenses a predetermined amount of particles on the pulp fluff in each mold. These particles are applied in a pattern that is phased with the molds to form the high absorbency zone such that the high absorbency zone is substantially centered in the mold. Preferably, the high absorbency zone is spaced at least 3 mm inwardly from the peripheral edges of the mold. Most preferably, the high absorbency zone is spaced at least 7 mm inwardly from the peripheral edges of the mold and therefore, also at least 7 mm from the peripheral edges of the absorbent element contained therein. Although the pattern shown in this embodiment is generally rectangular, the shape of the pattern is not limited to rectangular. Any shape of pattern may be used and one of ordinary skill in the are will discern that varying pattern shapes may be desirable or even preferable for varying shapes and types of structures to which the particles are applied.

The molds then enter the final fiber deposition zone 60 wherein additional pulp covers the high absorbency zone thereby forming an integral absorbent element. The molds are slightly overfilled with pulp, and two scarfing brushes 61 are used to make the pulp even with the top of the mold. The absorbent elements are then vacuum transferred out of the molds onto the vacuum transfer drum 62, from which they may then be transferred to another forming station for incorporation into absorbent products.

FIGS. 7A, 7B, 8A, 8B, and 9, illustrate the operation of the rotary particle applicator valve 59 in the particle application zone 58 in greater detail.

Figure 7A:
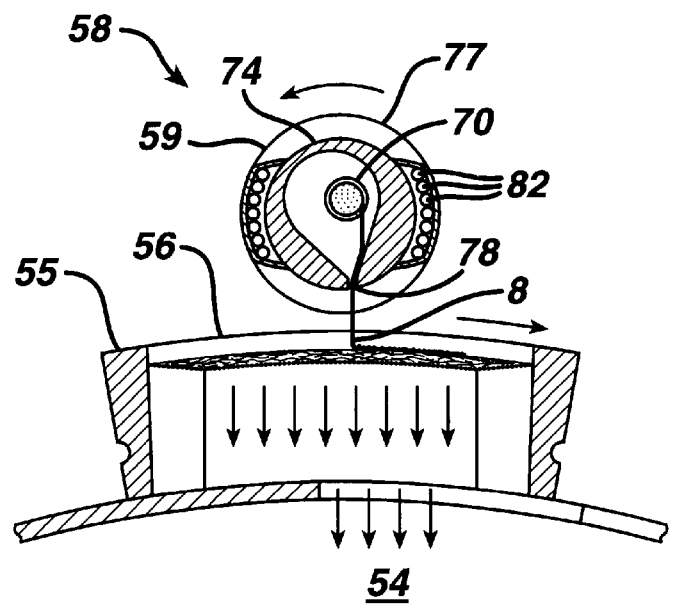
FIG. 7A is a detailed axial view of the particle rotary applicator of the apparatus shown in FIG. 6 in the particle application phase.
Figure 7B:
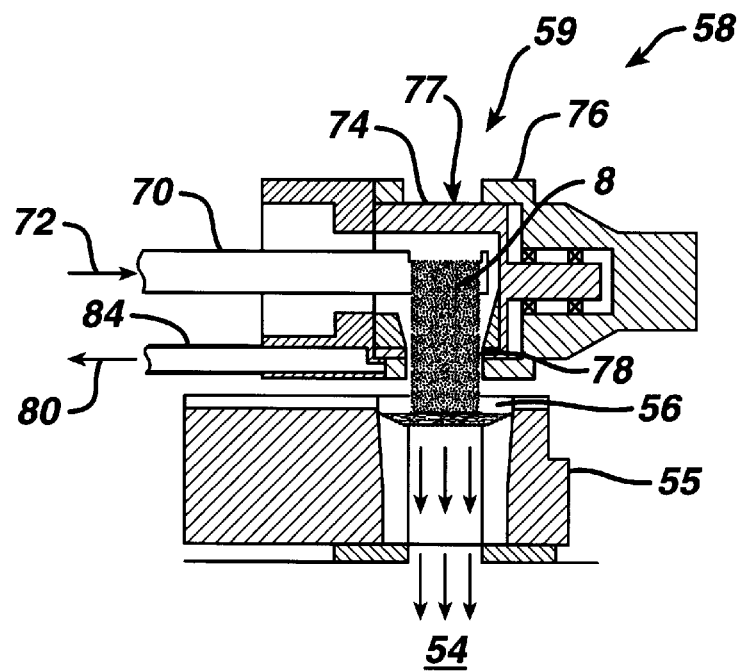
FIG. 7B is a detailed side view of the particle rotary applicator of the apparatus shown in FIG. 6 in the particle application phase.

FIGS. 7A and 7B show an axial view and a side view respectively of the rotary particle applicator valve 59 in the particle application phase. In order to achieve a precise pattern of particles on each mold 56, rotary particle applicator valve 59 is used as a means to start and stop the flow of particles to the molds 56. Particles are delivered to the rotary particle applicator valve 59 in the particle application zone 58. Preferably, the particles are delivered via a gravimetric feeder, such as a loss-in-weight (LIW) screw feeder 70 to accurately control the particle weight applied to each mold 56. However, other devices may also be used to supply measured amounts of particles to the rotary particle application valve, such as, for example, volumetric feed devices, in which the particle quantities are measured by volume. The particle supply source 72 is located outside of the particle application zone. The discharge end of the screw feeder 70 is located within a stationary funnel 74 of the rotary particle application valve. The stationary funnel is housed within the rotor housing 76 of the rotary particle application valve. The rotor housing 76 comprises at least one rotor slot opening 77. The stationary funnel 74 comprises one funnel slot opening 78. The widths of the stationary funnel 74, the rotor slot opening 77, the funnel slot opening 78, and the discharge end of the screw feeder 70 are matched to the width of the desired pattern of particles to be formed on each mold. As the rotor housing 76 turns, and the rotor slot opening 77 aligns with the funnel slot opening 78, the superabsorbent polymer particles 8 pass through the aligned openings and are deposited onto the mold 56. In the preferred apparatus, where the loss-in-weight screw feeder 70 is used, the particles simply fall through the openings onto the mold 56. The forming wheel vacuum 54 assists with the drawing of the particles downward onto the mold 56. Preferably, a portion of the screen bottom of each mold 56 is also masked such that an opening remains having the desired pattern shape. This selective masking of the molds enhances the accurate and precise placement of the particles within the mold. The length of the rotor slot opening 77 dictates the length of the pattern of particles forming the high absorbency zone 2 of the absorbent element 1.

Figure 8A:
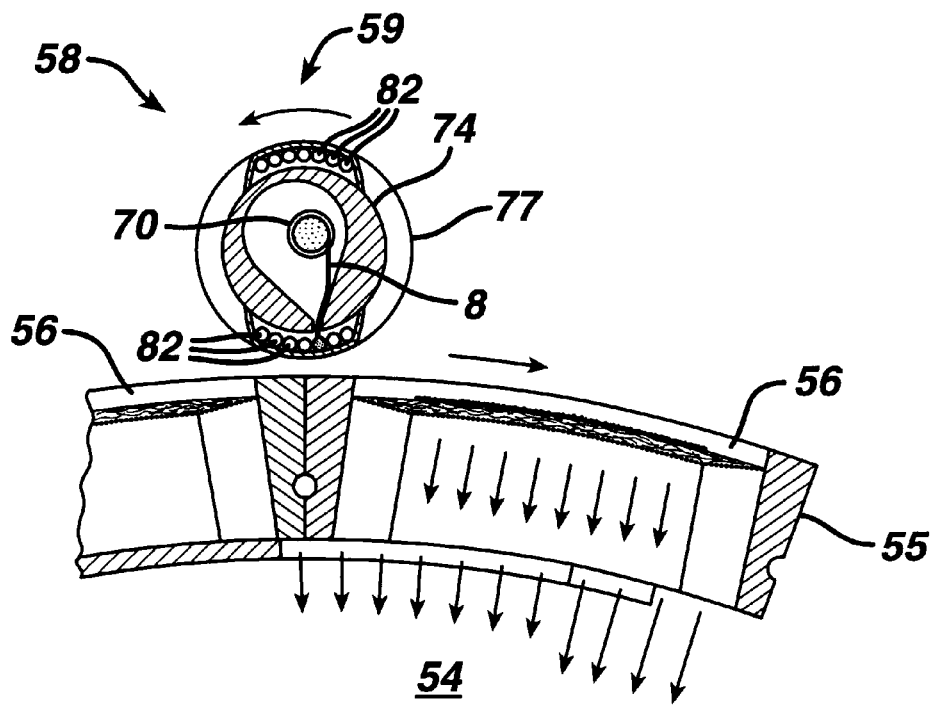
FIG. 8A is a detailed axial view of the particle rotary applicator of the apparatus shown in FIG. 6 in the recycle phase.
Figure 8B:
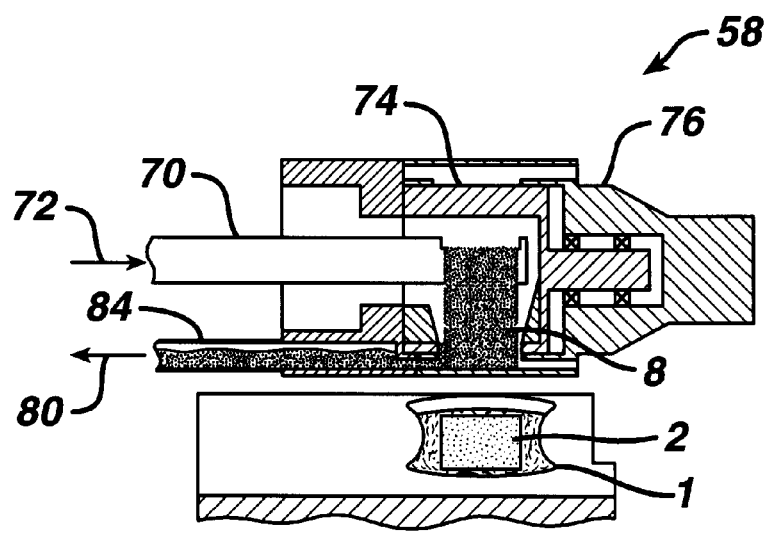
FIG. 8B is a detailed side view of the particle rotary applicator of the apparatus shown in FIG. 6 in the phase.
Figure 9:
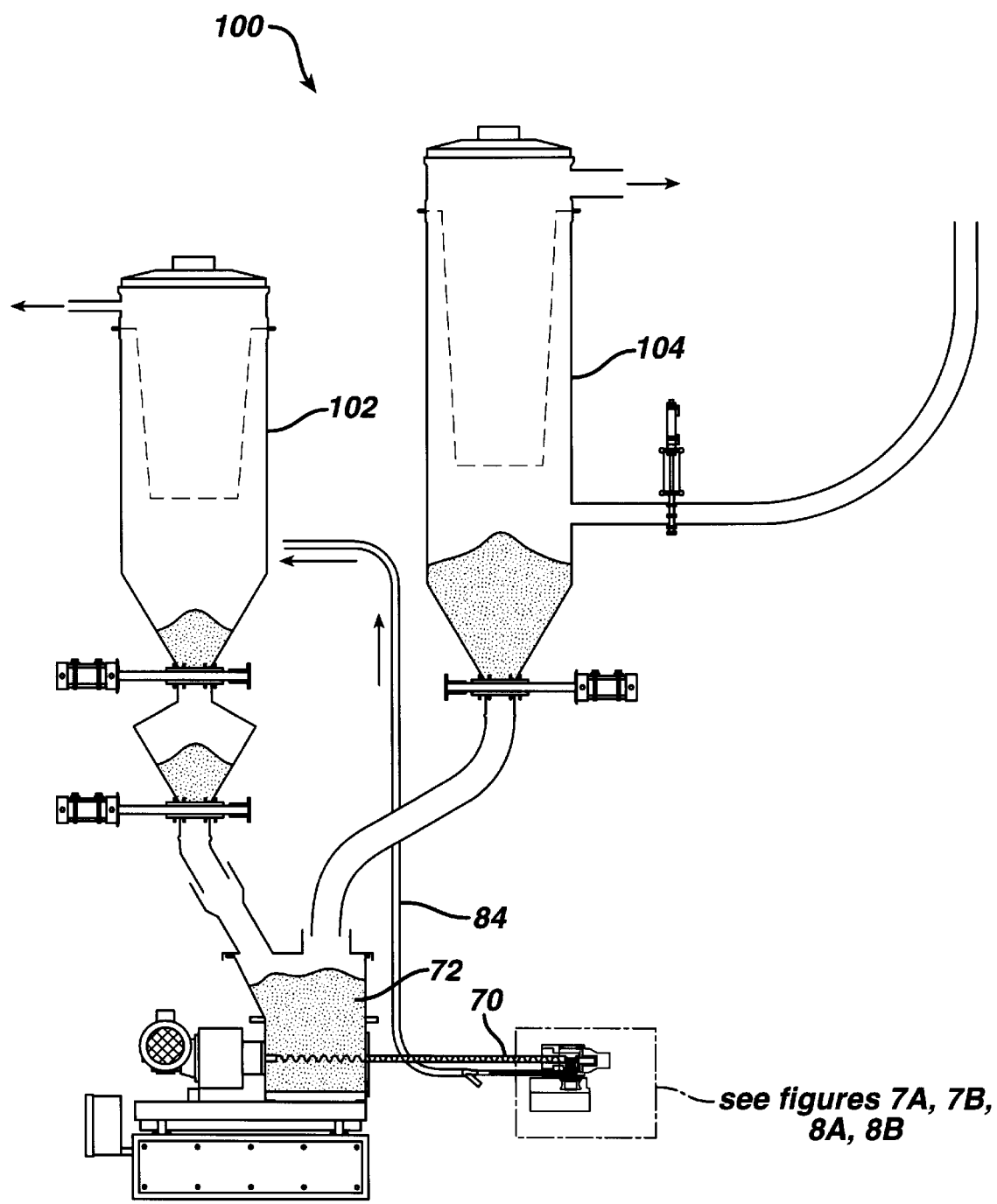
FIG. 9 is a detailed view of the gravimetric feeder and powder receivers to supply the particle rotary applicator of the apparatus shown in FIG. 6.

FIGS. 8A and 8B show an axial view and a side view respectively of the rotary particle applicator valve 59 in the recycle phase. In FIGS. 8A and 8B, the forming wheel 55 is shown in a position such that the rotary particle applicator valve 59 is located over a portion of the wheel between two molds 56. It is desired to prevent the deposition of particles over this portion of the wheel, since any particles dispensed in this position are essentially wasted and serve only to contaminate the area surrounding the apparatus. Product design may also dictate areas in the mold where the deposition of particles should be avoided. The recycle phase shown in FIGS. 8A and 8B prevents the problems associated wit unwanted disposition of particles by recycling the particles. When the Rotary Particle Applicator valve 59 is in the recycle phase as shown, the position of the rotor housing 76 under the stationary funnel 74 prevents the passage of particles; i.e., the rotor slot opening 77 is in a closed position. Particles exiting the screw feeder 70 then exit through the funnel slot opening 78 and hit the inside diameter of the rotor. A vacuum port 80 in the side of the rotor housing opens to the rotor housing inside diameter through a series of recycle holes 82 in he rotor housing and pulls the particles out of the rotor housing and into a recycling tube 84. As shown in FIG. 9, the particles are then conveyed by air through the recycling tube 84 to a recycle receiver 102 that will eventually provide the particles back to the screw feeder 70 for reuse. Also shown in FIG. 9 is a detailed view of the particle supply source 72, including both the virgin particle supply reservoir 104 and the recycle receiver 102.

Figure 12:
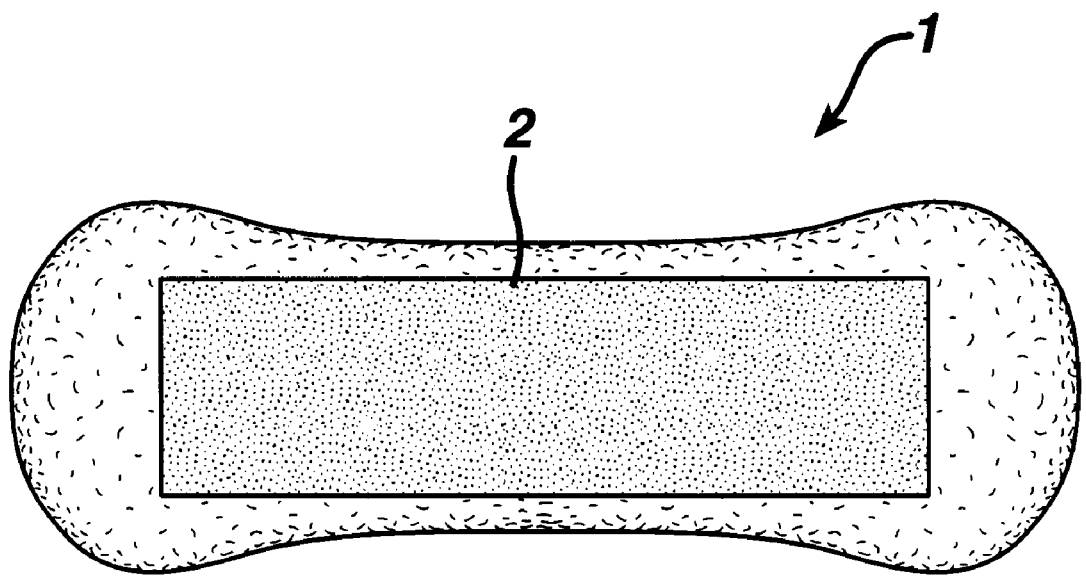
FIG. 12 is a plan view of a first embodiment of an absorbent element made by the method and apparatus of the invention.

FIG. 12 shows a simplified plan view of an absorbent element 1 made by the process, including the high absorbency zone 2. The length and width of the high absorbency zone are determined by the length and width of the rotor slot opening 77.

Figure 13:
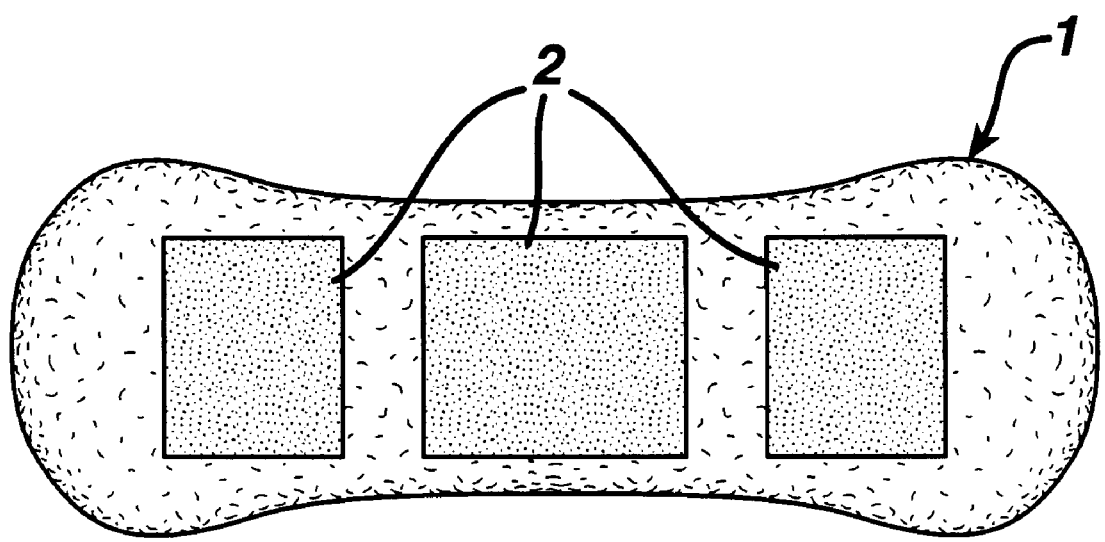
FIG. 13 is a plan view of a second embodiment of an absorbent element made by the method and apparatus of the invention.

The use of a rotor with a multiplicity of closely spaced, short rotor slot openings 77 would result in the formation of multiple high absorbency zones 2 along the longitudinal direction of absorbent element 1, as shown in FIG. 13.

FIGS. 10A, 10B, 11A, 11B, 14A, 14B, 15A, and 15B illustrate alternative embodiments of the apparatus of the invention. FIGS. 10A, 10B, 11A, and 11B illustrate the operation of a linear oscillating particle applicator valve 90 in the particle application zone 58 in greater detail. Likewise, FIGS. 14A, 14B, 15A, and 15B illustrate the operation of a rotary oscillating particle applicator valve 91 in the particle applicator zone 58 in greater detail.

Figure 10A:
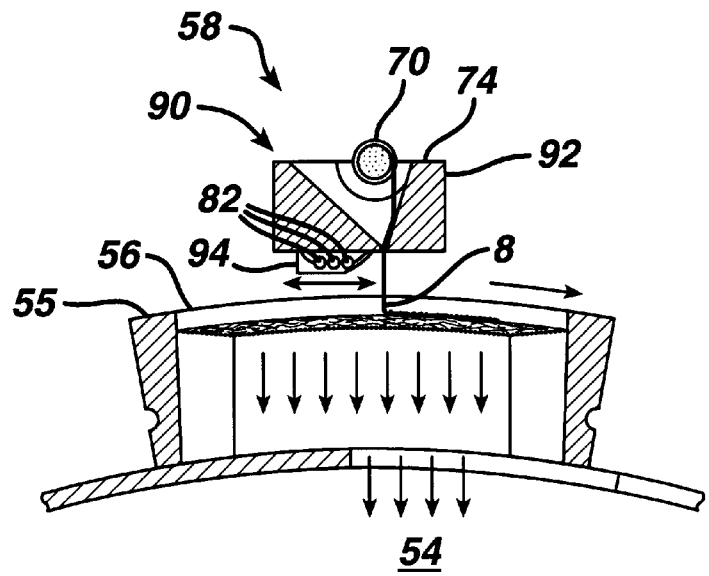
FIGS. 10a and 10b are cross-sectional views of the linear oscillation apparatus of the invention in the powder application phase.
Figure 10B:
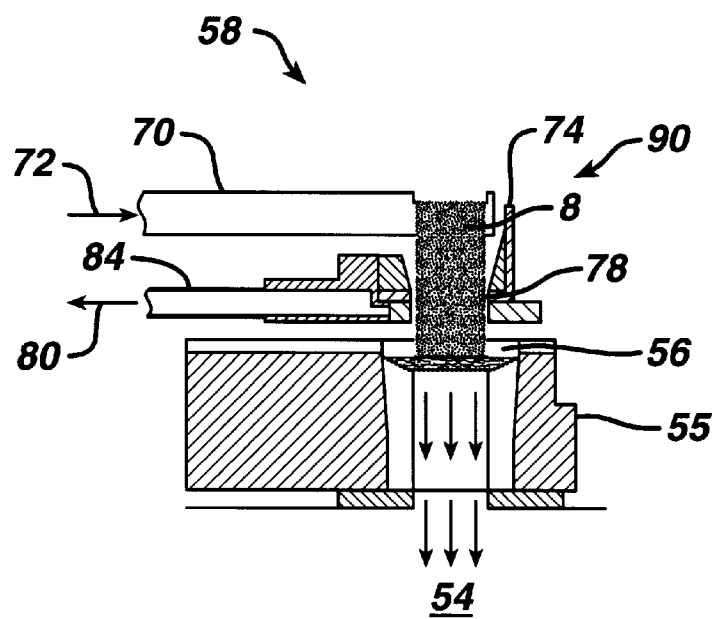
Figure 14A:
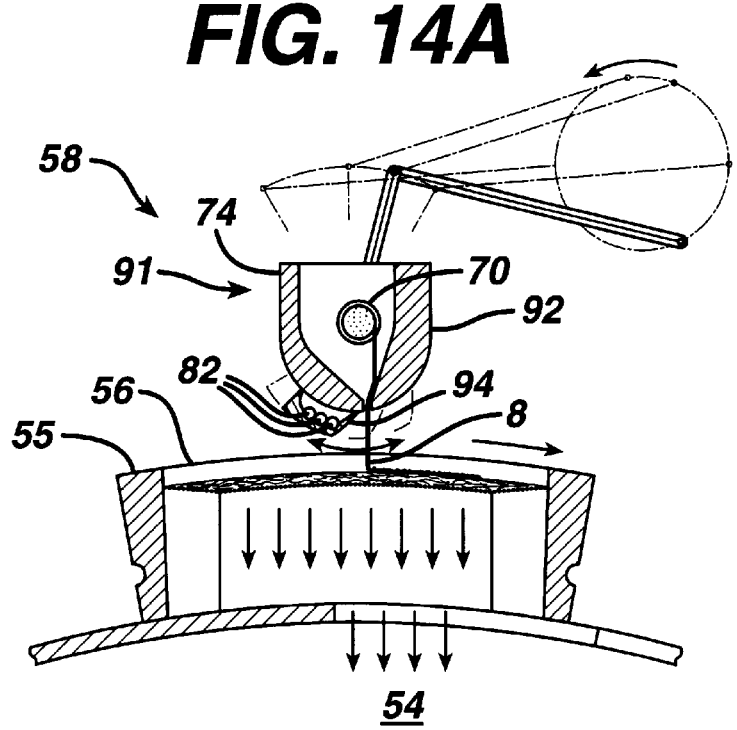
FIGS. 14a and 14b are cross-sectional views of the rotary oscillation apparatus of the invention in the powder application phase.
Figure 14B:
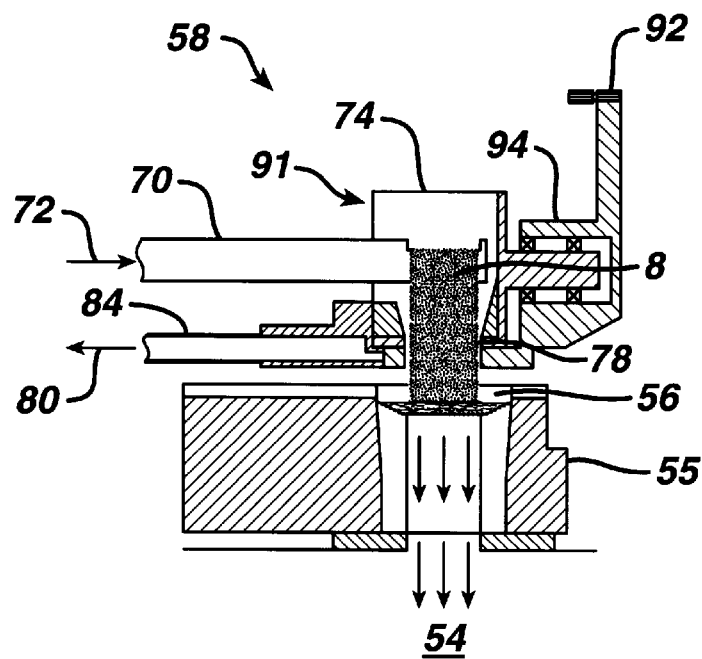

FIGS. 10A and 10B show an axial view and a side view respectively of the linear oscillating particle applicator valve 90, and FIGS. 14A and 14B show an axial view and a side view respectively of the rotary oscillating particle applicator valve 91 in the particle application phase. In order to achieve a precise pattern of particles on each mold 56, the oscillating particle applicator valve is used as a means to start and stop the flow of particles to the molds 56. Particles are delivered to the oscillating particle applicator valve in the particle application zone 58. Preferably, he particles are delivered via a gravimetric feeder, such as a loss-in-weight (LIW) screw feeder 70 to accurately control the particle weight applied to each mold 56. However, other devices may also be used to supply measured amounts of particles to the oscillating particle application valve, such as, for example, volumetric feed devices, in which the particle quantities are measured by volume. The particle supply source 72 is located outside of the particle application zone. The discharge end of the screw feeder 70 is located within a stationary funnel 74 of the oscillating particle application valve. The stationary funnel is housed within the oscillating valve housing 92 of the oscillating particle application valve. The oscillating valve housing 92 also comprises a gate valve 94. The gate valve 94 comprises a series of recycle holes 82. The stationary funnel 74 comprises at least one slot opening 78. The widths of the stationary funnel 74, the slot opening 78, and the recycle holes 82 are matched to the width of the desired pattern of particles to be formed on each mold. As the oscillating gate valve 94 moves in a linear direction, and the funnel slot opening 78 is uncovered by the gate valve 94, i.e., the gate valve 94 is in an open position, the superabsorbent polymer particles 8 pass through the funnel opening 78 and are deposited onto the mold 56. In the preferred apparatus, where the loss-in-weight screw feeder 70 is used, the particles simply fall by gravity through the openings onto the mold 56. The forming wheel vacuum 54 assists with the drawing of the particles downward onto the mold 56. Preferably, a portion of the screen bottom of each mold 56 is also masked such that an opening remains having the desired pattern shape. This selective masking of the molds enhances the accurate and precise placement of the particles within the mold. The length of time that the slot 78 is open dictates the length of the pattern of particles forming the high absorbency zone 2 of the absorbent element 1.

Figure 11A:
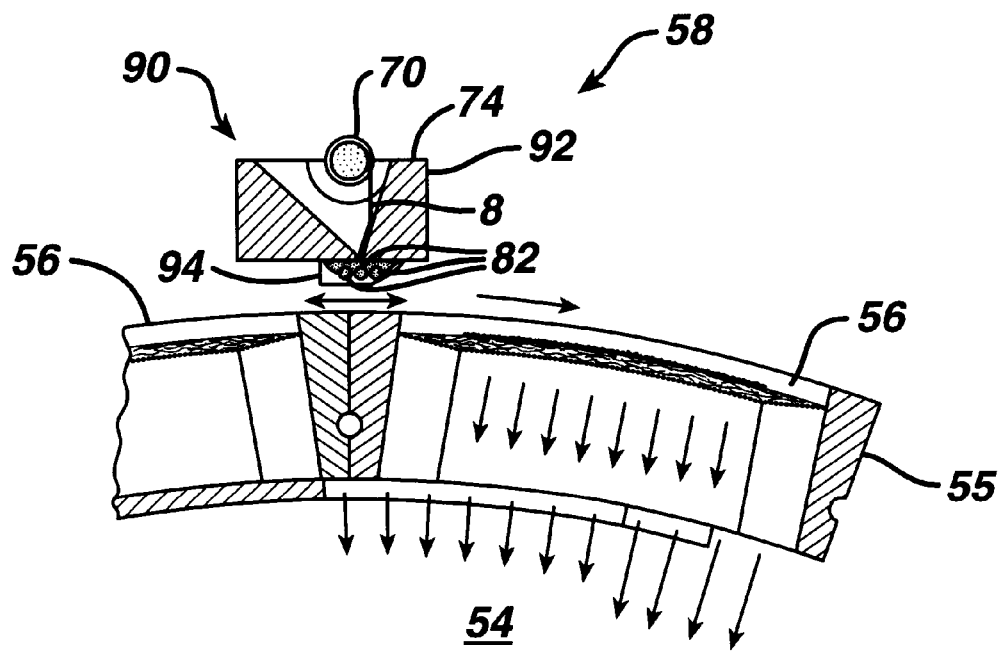
FIGS. 11a and 11b are cross-sectional views of the linear oscillation apparatus of the invention in the recycle phase.
Figure 11B:
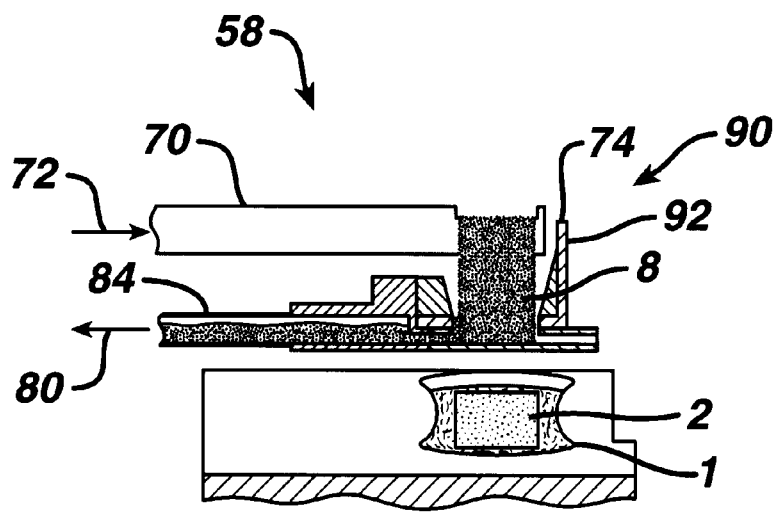
Figure 15A:
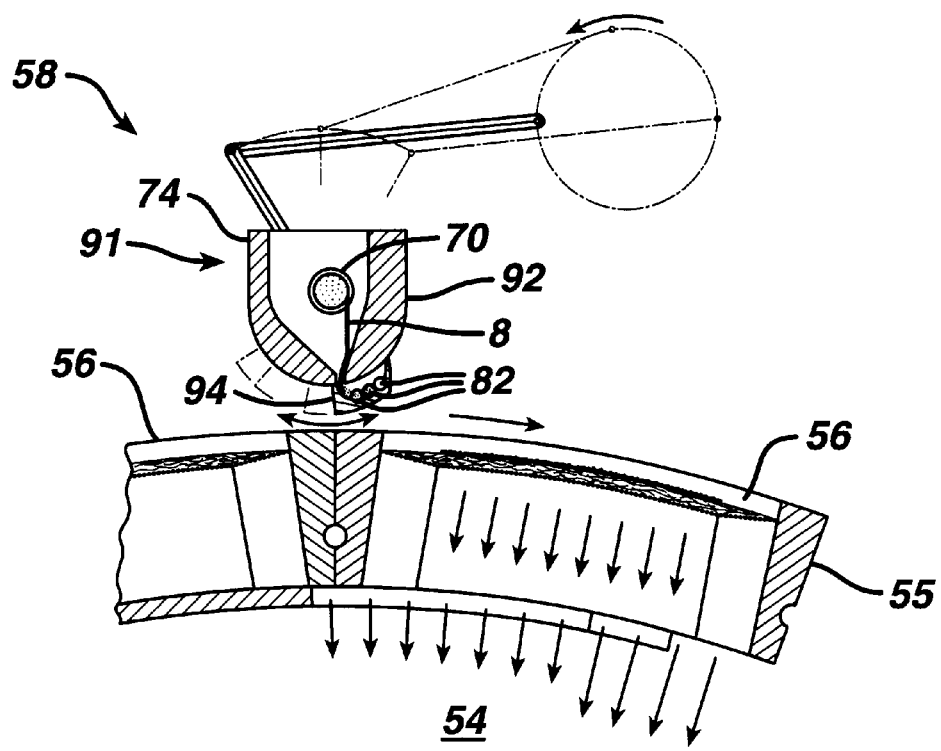
FIGS. 15a and 15b are cross-sectional views of the rotary oscillation apparatus of the invention in the recycle phase.
Figure 15B:
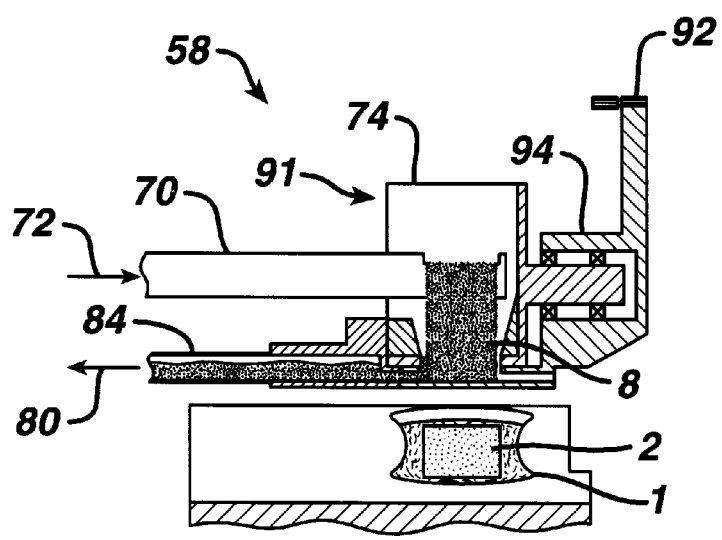

FIGS. 11A and 11B show an axial view and a side view respectively of the linear oscillating particle applicator valve 90, and FIGS. 15A and 15B show an axial view and a side view respectively of the rotary oscillating particle applicator valve 91 in the recycle phase. In FIGS. 11A, 11B, 15A, and 15B the forming wheel 55 is shown in a position such that the oscillating particle applicator valve is located over a portion of the wheel between two molds 56. It is desired to prevent the deposition of particles over this portion of the wheel since any particles dispensed in this position are essentially wasted and serve only to contaminate the area surrounding the apparatus. End-product absorbent article design may also dictate areas in the mold where the deposition of particles should be avoided. The recycle phase shown in FIGS. 11A, 11B, 15A, and 15B prevents the problems associated with unwanted deposition of particles by recycling the particles. When the oscillating particle applicator valve is in the recycle phase as shown, the position of the oscillating gate valve 94 under the stationary funnel 74 prevents the passage of particles; i.e., the slot opening 78 is in a closed position. Particles exiting the screw feeder 70 then exit through the stationary funnel slot 78 and hit the inside surface of the oscillating gate valve 94. A vacuum port 80 in the side of the oscillating valve housing 92 opens to the housing inside diameter through a series of recycle holes 82 in the housing and pulls the particles out of the housing and into a recycling tube 84. As shown in FIG. 9, he particles are then conveyed by air through the recycling tube 84 to a recycle receiver 102 that will eventually provide the particles back to the screw feeder 70 for reuse. Also shown in FIG. 9 is a detailed view of the particle supply source 72, including both the virgin particle supply reservoir 104 and the recycle receiver 102.

FIG. 12 shows a simplified plan view an absorbent element 1 made by the process, including the high absorbency zone 2. The width of the high absorbency zone is determined by the width of the slot opening 78. The length of the high absorbency zone is determined by the length of time that the slot 78 is open.

Control of the timing and frequency of oscillation of the gate valve would result in the formation of multiple high absorbency zones 2 along the longitudinal direction of absorbent element 1, as shown in FIG. 13.

EXAMPLE

An absorbent element was formed according to a preferred embodiment of the method and apparatus of this invention as illustrated in FIG. 6 and as described herein, in which a pulp board was defiberized and dispersed into individual fibers in a hammer mill. The pulp fibers was entrained in a stream of air and enough of the fibers were deposited into a shaped screen-bottomed mold to cover the screen with about a one (1) millimeter thickness of pulp fluff. A predetermined amount of CHEMDAL 200™ superabsorbent polymer particles was then deposited in a 35 millimeter wide stripe along a central portion of the mold. The amount of superabosorbent polymer particles (SAP) was either 0 grams, 0.2 gram, 0.4 gram, or 0.7 gram per mold. Since the deposition of superabsorbent polymer particles per mold was substantially evenly disposed along a 35 mm wide stripe on the absorbent element, and since the superabsorbent polymer particles tended in general to be somewhat more dense than pulp fluff fibers, the superabsorbent polymer particles tended to lodge in the spaces between pulp fluff fibers as they were dispensed onto the 1 mm thickness of pulp fluff. Finally, additional pulp fibers were added to he mold to form a pad with a total pulp weight of 8.0 grams and a total weight of superabsorbent polymer particles as provided in Table 1.

The absorbent element was removed from the mold and oriented so that the surface of the element which had contacted the screen was the first or top surface of the element. The resulting element had a generally oblong shape with a length of about 200 millimeters and a width of about 60 millimeters. Each element was between 7 mm and 20 mm in thickness with a density of less than 0.07 g/cc.

Figure 5:
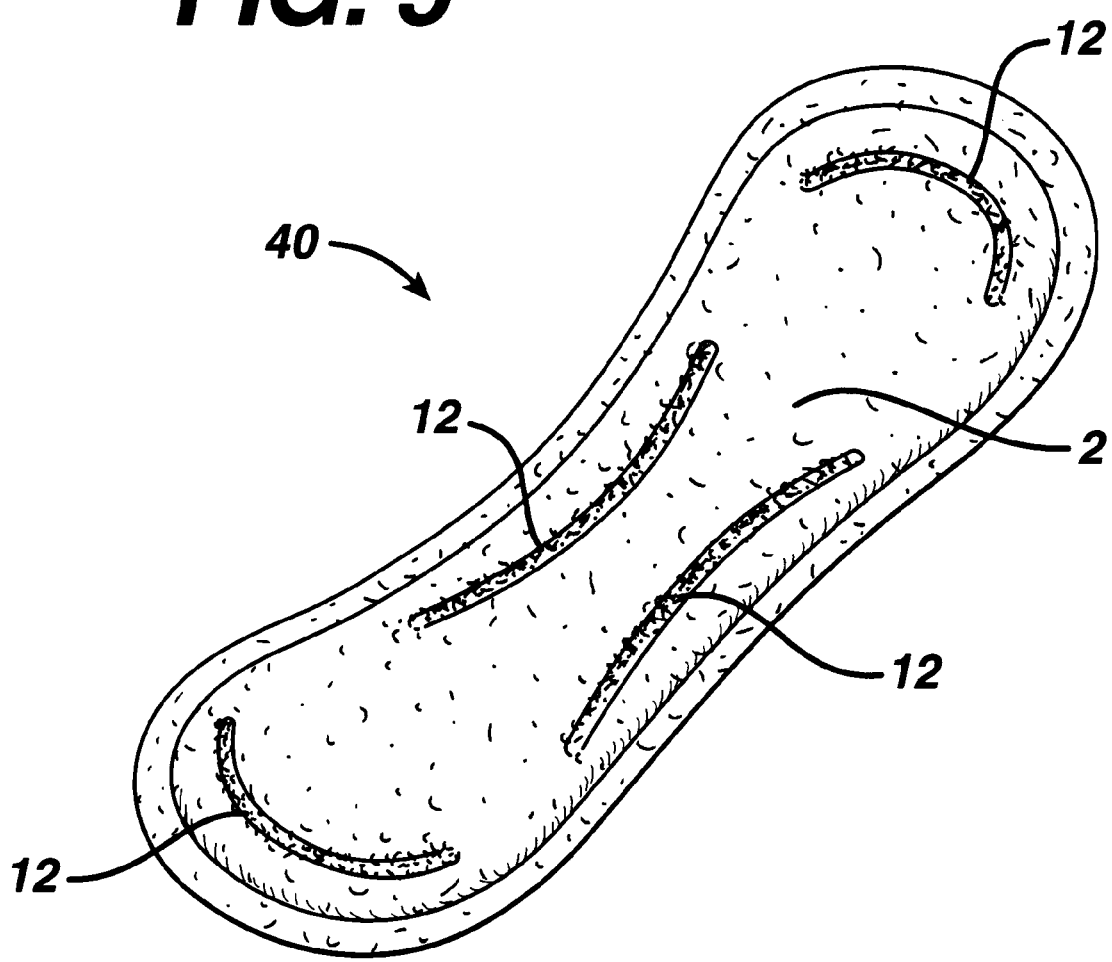
FIG. 5 is a perspective view of a preferred embodiment of an absorbent article made by the method and apparatus of the invention.

Each element was then placed between a cover layer comprising a homogeneous blend of 50% of 5denier polypropylene staple fibers and 50% of 3 denier polypropylene staple fibers, and a barrier layer of 0.001 inch thick polyethylene film with the cover layer being placed on the first surface of the element. The cover and barrier were sealed to one another around the edges of the element to form a flange seal. Densified side channels were then formed in the first (cover layer) surface of the article by heating and compressing the cover/absorbent element/barrier assembly in selected areas to form densified channels similar to those shown in FIG. 5. The density of the channels was at least 0.5 g/cc.

The resulting articles were then tested for strikethorugh times and rewet amounts. Strikethrough times indicate the amount of time that is required for each of six 2 cc aliquots of test fluid to penetrate the cover, where lower numbers indicate faster fluid penetration and thus, less gel-blocking. Rewet amounts indicate the amount of absorbed test fluid that may be squeezed out through the cover of the article when pressure is applied. Lower rewet amounts indicate that the absorbed fluid is being retained well, thus leading to a drier feeling product in use.

The strikethrough time was measured by the following method. A 2.54 cm thick plate with a 2 cm round hole was placed over the cover of the article with the hole aligned with the center of the article. A 2 cc dose of synthetic menstrual fluid was deposited in the hole and the time required for it to absorb into the article (i.e., penetration time) was measured. Five additional 2 cc doses were added at 5 minute intervals and the penetration time was measured for each one. The penetration times for the first and sixth doses are shown in Table 1. The increases in penetration time for the sixth dose with 0.4 and 0.7 gram SAP addition are evidence of gel blocking.

For the rewet test, a 2.54 cm thick orifice plate with a centrally located 3.8 cm by 1.9 cm elliptical aperture was placed over the article with the aperture aligned with the center of the article. A 7 cc dose of synthetic menstrual fluid was deposited in the aperture and allowed to penetrate the article. After 15 minutes a pre-weighed stack of four sheets of Whatman @1 filter paper was placed over the article sample. A 2.2 kg weight was placed over the filter paper for three (3) minutes. The filter paper was then removed and weighed. The amount of fluid picked up by the filter paper was calculated and reported as the rewet amount.

The test fluid used for the penetration test and the rewet test may be any synthetic menstrual fluid having a viscosity of approximately 30 centipoise. The results of the tests are indicated in Table I below.

TABLE I

| 35 mm Wide strip of SAP along length of element 8.0 Gram Pulp | | | | |
|---|---|---|---|---|
| Amt. SAP (grams) | Amt. SAP (gsm) | Rewet Value (grams) | Penetration ($1^{st}$ dose-sec) | Penetration ($6^{th}$ dose-sec)) |
| 0 | 0 | 0.027 | 6 | 13 |
| 0.2 | 30 | 0.019 | 6 | 13.0 |
| 0.4 | 60 | 0.021 | 6 | 24 |
| 0.7 | 103 | 0.025 | 6.5 | 31 |

As can be seen from the data in Table I, the formation of an integral high absorbency zone comprising superabsorbent polymer improved the rewet amounts, with the 30 gsm loading of superabsorbent leading to the best (lowest) rewet amount. Slightly higher rewet was measured at 60 gsm. At 103 gsm, the rewet was not improved substantially compared to the structure without SAP, and the penetration time was sharply increased. Therefore, it was discovered that for the absorbent structure of the present invention, a superabsorbent loading of between 30–55 gsm is preferred for improving rewet amount without gel-blocking. Some rewet benefit may also be obtained at SAP add-ons of up to 75 gsm.

The specification and embodiments above are presented to aid in the complete and non-limiting understanding of the invention disclosed herein. Since many variations and embodiments of the invention can be made without departing from its spirit and scope, the invention resides in the claims hereinafter appended.

We claim:

1. A method of applying particulate material to a substrate, the method comprising the steps of:

providing a substrate;

providing a continuous supply of particulate material from a supply source to a valve having a powder application phase and a recycle phase;

disposing the valve to the powder application phase to allow passage of the particulate material by free-fall therethrough and to prevent conveying of the particulate material to the supply source;

dispensing a measured amount of the particulate material through the valve onto at least a portion of a surface of the substrate;

disposing the valve to the recycle phase to prevent dispensing of the particulate material onto the substrate and allow passage therethrough to the supply source; and conveying the particulate material back to the supply source.

2. The method of claim 1 wherein the valve is a rotary valve moving at constant revolutions in one direction.

3. The method of claim 1 wherein the valve is a linear oscillating gate valve.

4. The method of claim 1 wherein the valve is a rotary oscillating gate valve.

5. The method of claim 1 wherein the measured amount of particulate material falls by gravity onto the substrate.

6. The method of claim 1 wherein the supply source is a gravimetric feeder.

7. The method of claim 3 wherein the gravimetric feeder is a loss-in-weight screw feeder.

8. The method of claim 1 wherein the particulate material is super absorbent particles.

9. A method of applying particulate material to an absorbent substrate, the method comprising the steps of:

providing an absorbent substrate;

providing a continuous supply of particulate material from a supply source to a valve having a powder application phase and a recycle phase;

disposing the valve to the powder application phase to allow passage of the particulate material by free-fall therethrough and to prevent conveying of the particulate material to the supply source;

dispensing a measured amount of the particulate material through the valve onto at least a portion of a surface of the absorbent substrate;

disposing the valve to the recycle phase to prevent dispensing of the particulate material onto the absorbent substrate and allow passage therethrough to the supply source; and conveying the particulate material back to the supply source.

10. A method applying particulate material to a substrate, the method comprising the steps of:

providing a substrate;

providing a continuous supply of particulate material from a supply source to a rotary valve having a powder application phase and a recycle phase;

disposing the rotary valve to the powder application phase to low passage of the particulate material by free-fall therethrough and to prevent conveying of he particulate material to the supply source;

dispensing a measured amount of the particulate material through the rotary valve onto at least a portion of a surface of the substrate;

disposing the rotary valve to the recycle phase to prevent dispensing of the particulate material onto the substrate and allow passage therethrough to the supply source; and conveying the particulate material back to the supply source.

11. A method of applying particulate material to a substrate, the method comprising the steps of:

providing a substrate;

providing a continuous supply of particulate material from a supply source to a linear oscillating valve having a powder application phase and a recycle phase;

disposing the linear oscillating valve to the powder application phase to allow passage of the particulate material by free-fall therethrough and to prevent conveying of the particulate material to the supply source;

dispensing a measured amount of the particulate material through the linear oscillating valve onto at least a portion of a surface of the substrate;

disposing the linear oscillating valve to the recycle phase to prevent dispensing of the particulate material onto the substrate and allow passage therethrough to the supply source; and conveying the particulate material back to the supply source.

* * * * *

UNITED STATES PATENT AND TRADEMARK OFFICE
CERTIFICATE OF CORRECTION

PATENT NO. : 6,139,912
DATED : October 31, 2000
INVENTOR(S) : Anthony David Onuschak and Fernando Ydoate Page 1 of 1

It is certified that error appears in the above-identified patent and that said Letters Patent is hereby corrected as shown below:

Column 16,
Line 5, "low" should be "allow"

Signed and Sealed this

Thirtieth Day of October, 2001

*Attest:*

NICHOLAS P. GODICI
*Attesting Officer*  *Acting Director of the United States Patent and Trademark Office*